(12) United States Patent
Sato et al.

(10) Patent No.: US 11,406,309 B2
(45) Date of Patent: Aug. 9, 2022

(54) HEARTBEAT RATE CALCULATION DEVICE AND METHOD

(71) Applicant: Nippon Telegraph and Telephone Corporation, Tokyo (JP)

(72) Inventors: Rieko Sato, Tokyo (JP); Nobuaki Matsuura, Tokyo (JP); Kei Kuwabara, Tokyo (JP); Takayuki Ogasawara, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 88 days.

(21) Appl. No.: 16/978,031

(22) PCT Filed: Mar. 1, 2019

(86) PCT No.: PCT/JP2019/008061
§ 371 (c)(1),
(2) Date: Sep. 3, 2020

(87) PCT Pub. No.: WO2019/172111
PCT Pub. Date: Sep. 12, 2019

(65) Prior Publication Data
US 2021/0000366 A1  Jan. 7, 2021

(30) Foreign Application Priority Data

Mar. 6, 2018 (JP) .............................. JP2018-039446
Apr. 19, 2018 (JP) .............................. JP2018-080426

(51) Int. Cl.
*A61B 5/00* (2006.01)
*A61B 5/316* (2021.01)
*A61B 5/304* (2021.01)
*A61B 5/0245* (2006.01)

(52) U.S. Cl.
CPC ............ *A61B 5/316* (2021.01); *A61B 5/0245* (2013.01); *A61B 5/304* (2021.01); *A61B 5/725* (2013.01)

(58) Field of Classification Search
CPC ....... A61B 5/316; A61B 5/0245; A61B 5/304; A61B 5/725; A61B 5/7203; A61B 5/364; A61B 5/352; A61B 5/02; A61B 5/024; A61B 5/349; A61B 5/346
See application file for complete search history.

(56) References Cited

PUBLICATIONS

Yang et al., "Adaptive Change Detection in Heart Rate Trend Monitoring in Anesthetized Children," IEEE Transactions on Biomedical Engineering, vol. 53, No. 11, Nov. 2006, pp. 2211-2219.

(Continued)

*Primary Examiner* — Scott M. Getzow
(74) *Attorney, Agent, or Firm* — Slater Matsil, LLP (57) ABSTRACT

A first calculation unit calculates the heart rate of a subject from a plurality of instantaneous heart rates by averaging processing with an IIR filter using a first coefficient. Note that the first coefficient is a numerical value less than 1, and is a fixed value. A second calculation unit calculates the heart rate of the subject from the plurality of instantaneous heart rates by averaging processing with an IIR filter using a second coefficient. The second coefficient is a numerical value less than 1, and is a variable value. A switching unit switches between the first calculation unit and the second calculation unit based on a difference between the precedingly calculated heart rate and a latest instantaneous heart rate.

22 Claims, 6 Drawing Sheets

(56) References Cited

PUBLICATIONS

Chulsung Park et al., "An Ultra-Wearable, Wireless, Low Power ECG Monitoring System," Biomedical Circuits and Systems Conference, 2006. BioCAS 2006, Californian, USA, IEE, 4 pages. As discussed in the specification.

HEARTBEAT RATE CALCULATION DEVICE AND METHOD

CROSS-REFERENCE TO RELATED APPLICATIONS

This application is a national phase entry of PCT Application No. PCT/JP2019/008061, filed on Mar. 1, 2019, which claims priority to Japanese Patent Application No. 2018-039446, filed on Mar. 6, 2018 and Japanese Patent Application No. 2018-080426, filed on Apr. 19, 2018, which applications are hereby incorporated herein by reference.

TECHNICAL FIELD

The present invention relates to a heartbeat count calculation apparatus and method for calculating a heartbeat count such as a heart rate or a pulse rate and, particularly, to a heartbeat count calculation apparatus and method capable of stably calculating a heartbeat count even if instantaneous heartbeat counts include an abnormal value.

BACKGROUND

Measurement of a heart rate fluctuation is useful to control the loading intensity of the cardiopulmonary function. In recent years, a wearable device that can measure an electrocardiogram by incorporating an electrode in clothing such as a shirt has been developed. Thus, in various scenes, a heart rate fluctuation is monitored and observed.

RELATED ART LITERATURE

Non-Patent Literature

Non-Patent Literature 1: C. Park et al., "An Ultra-Wearable, Wireless, Low Power ECG Monitoring System", Biomedical Circuits and Systems Conference, 2006. BioCAS 2006. IEEE.

SUMMARY

Disclosure of Embodiments of the Invention

Problem to be Solved by Embodiments of the Invention

However, a wearable heart rate measurement device may lead a heart rate detection error since noise is readily added to a measurement result (electrocardiographic waveform). As a result, instantaneous heart rates for respective beats obtained in time series from the measured electrocardiographic waveform include an abnormal value. To prevent calculation of such abnormal value, it is important to appropriately average the instantaneous heart rates obtained from the measured electrocardiographic waveform.

As an averaging technique, for example, non-patent literature 1 describes a technique in which when calculating a heart rate from instantaneous heart rates obtained from an electrocardiographic waveform, the moving average of input data points is obtained until predetermined data points as moving average targets are input. However, processing when time-series data of the instantaneous heart rates include an abnormal value is not mentioned.

Since noise is readily added to an electrocardiographic waveform obtained using a wearable device to lead a heart rate detection error, instantaneous heart rates include an abnormal value. Therefore, to monitor the transition of the heart rate, it is important to obtain an appropriately averaged heart rate (instantaneous heart rate).

Embodiments of the present invention has been made in consideration of the above problems, and has as its object to calculate a heart rate appropriately even if instantaneous heartbeat counts concerning the heartbeat count of the heart, such as instantaneous heart rates, include an abnormal value.

Means of Solution to the Problem

According to embodiments of the present invention, there is provided a heartbeat count calculation apparatus comprising an extraction unit configured to extract a plurality of instantaneous heartbeat counts concerning a heartbeat count of a heart in time series from biometric information, a first calculation unit configured to obtain the heartbeat count from the plurality of instantaneous heartbeat counts by averaging processing with an IIR filter using a first coefficient of a fixed value smaller than 1, a second calculation unit configured to obtain the heartbeat count from the plurality of instantaneous heartbeat counts by averaging processing with an IIR filter using a second coefficient of a variable value smaller than 1, and a switching unit configured to switch between the first calculation unit and the second calculation unit based on a difference between the heartbeat count obtained by one of the first calculation unit and the second calculation unit and a latest instantaneous heartbeat count extracted by the extraction unit.

According to embodiments of the present invention, there is also provided a heartbeat count calculation method comprising a first step of extracting a plurality of instantaneous heartbeat counts in time series from an electrocardiographic waveform of a living body, a second step of obtaining a heartbeat count from the plurality of instantaneous heartbeat counts by averaging processing with an IIR filter using a first coefficient of a fixed value smaller than 1, a third step of obtaining a heartbeat count from the plurality of instantaneous heartbeat counts by averaging processing with an IIR filter using a second coefficient of a variable value smaller than 1, and a fourth step of switching between the second step and the third step based on a difference between an extracted latest instantaneous heartbeat count and the heartbeat count precedingly obtained in one of the second step and the third step.

Effect of Embodiments of the Invention

As described above, according to embodiments of the present invention, it is possible to obtain a great effect of calculating a heartbeat count appropriately even if instantaneous heartbeat counts include an abnormal value.

DETAILED DESCRIPTION OF ILLUSTRATIVE EMBODIMENTS

Best Mode for Carrying Out Embodiments of the Invention

Figure 1:
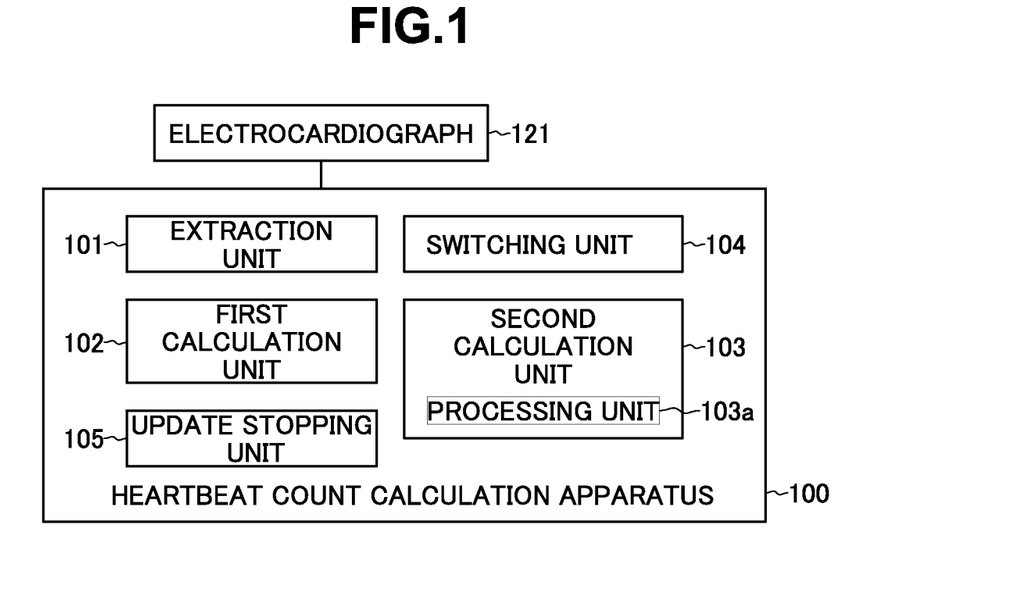
FIG. 1 is a block diagram showing the arrangement of a heartbeat count calculation apparatus according to an embodiment of the present invention.

A heartbeat count calculation apparatus 100 according to an embodiment of the present invention will be described below with reference to FIG. 1. The heartbeat count calculation apparatus 100 includes an extraction unit 101, a first calculation unit 102, a second calculation unit 103, and a switching unit 104.

The extraction unit 101 extracts a plurality of instantaneous heartbeat counts concerning the heartbeat count of the heart in time series from biometric information obtained from a target living body (subject). The biometric information is, for example, the electrocardiographic waveform of the subject obtained by measurement using an electrocardiograph 121, and the heartbeat count is a heart rate. As is well known, an instantaneous heart rate is obtained based on the R-R interval of the electrocardiographic waveform. If the R-R interval is 2 sec, an instantaneous heart rate is 30 times/min by calculating 60 sec/2. A heart rate will be exemplified as a heartbeat count.

The first calculation unit 102 obtains the heart rate (heartbeat count) of the subject from a plurality of instantaneous heart rates (instantaneous heartbeat counts) by averaging processing with an IIR (Infinite Impulse Response) filter using the first coefficient. Note that the first coefficient is a numerical value smaller than 1, and is a fixed value. The first calculation unit 102 updates the heart rate by obtaining the heart rates in time series by, for example, multiplying an instantaneous heart rate at a given time by the first coefficient, and adding, to the thus obtained value, a value obtained by multiplying an instantaneous heart rate at an immediately preceding time by a value obtained by subtracting the first coefficient from 1 [heart rate at current time=(instantaneous heart rate×first coefficient)+{heart rate at immediately preceding time×(1−first coefficient)}].

The second calculation unit 103 obtains the heart rate of the subject from the plurality of instantaneous heart rates by averaging processing with an IIR filter using the second coefficient. The second coefficient is a numerical value smaller than 1 and is a variable value. The second calculation unit 103 updates the heart rate by obtaining the heart rates in time series by, for example, adding, to a value obtained by multiplying the instantaneous heart rate by the second coefficient, a value obtained by multiplying the heart rate at the immediately preceding time by a value obtained by subtracting the second coefficient from 1. The second calculation unit 103 includes a processing unit 103a that starts the second coefficient with a value larger than the first coefficient and makes the second coefficient closer to the first coefficient for each beat. The calculation unit 103 uses the second coefficient having undergone coefficient processing by the processing unit 103a.

The switching unit 104 switches between the first calculation unit 102 and the second calculation unit 103 based on the difference between the precedingly obtained heart rate and the latest instantaneous heart rate. The switching unit 104 switches, from one of the first calculation unit 102 and the second calculation unit 103 to the other, a processing unit that is to obtain a heart rate output from the heartbeat count calculation apparatus. The switching unit 104 determines, based on the difference between the precedingly calculated heart rate and the latest instantaneous heart rate, whether to leave one of the calculation units that has calculated the heart rate last time as a processing unit to perform processing for calculating a heart rate using the latest instantaneous heart rate, or switch from the calculation unit to the other, and, when it has determined to switch the processing unit, the switching unit 104 switches the processing unit. The heartbeat count calculation apparatus outputs the heart rate calculated by the first calculation unit 102 or the second calculation unit 103 switched by the switching unit 104.

The switching unit 104 switches from the first calculation unit 102 to the second calculation unit 103 in, for example, the first state in which a state in which the difference between the latest instantaneous heart rate and the heart rate calculated by the first calculation unit 102 is equal to or larger than the set first constant continues during the set first heart count.

Furthermore, the switching unit 104 switches from the second calculation unit 103 to the first calculation unit 102 in, for example, the second state in which a state in which the difference between the latest instantaneous heart rate and the heart rate calculated by the second calculation unit 103 is equal to or smaller than the set second constant continues during the set second heartbeat count or the third state in which the second coefficient is equal to the first coefficient.

For example, if the first calculation unit 102 calculates the heart rate last time and the difference between this heart rate and the instantaneous heart rate extracted by the extraction unit 101 this time is in the first state, the switching unit 104 performs switching processing. In this case, the second calculation unit 103 calculates the heart rate this time. Alternatively, for example, if the second calculation unit 103 calculates the heart rate last time, and the difference between this heart rate and the instantaneous heart rate extracted by the extraction unit 101 this time is in the second or third state, the switching unit 104 performs switching processing. In this case, the first calculation unit 102 calculates the heart rate this time.

The heartbeat count calculation apparatus 100 according to the embodiment includes an update stopping unit 105 in addition to the above-described components. The update stopping unit 105 stops update of the heart rate when the difference between the latest instantaneous heart rate and the heart rate calculated by the first calculation unit 102 exceeds a set reference value, and limits the update value of the heart rate when the difference between the heart rate calculated at the current time by the first calculation unit 102 and that calculated at the immediately preceding time by the first calculation unit 102 exceeds the set reference value.

Figure 2:
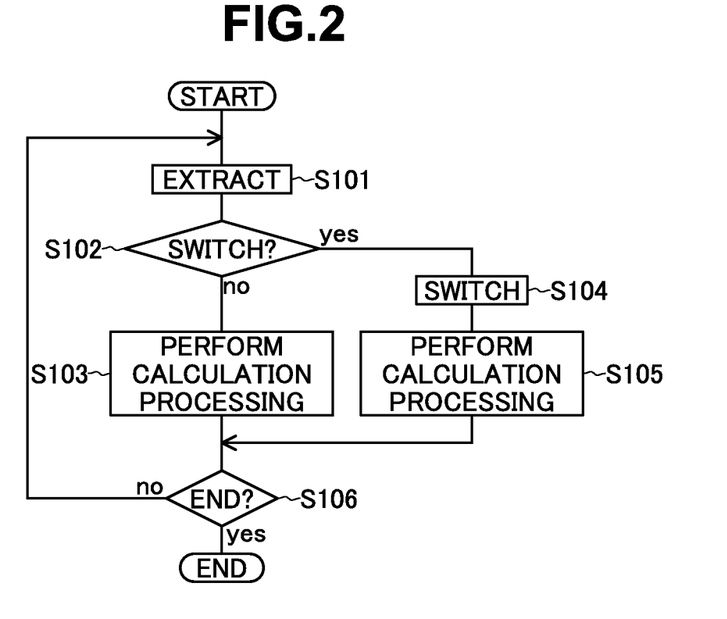
FIG. 2 is a flowchart for explaining a heartbeat count calculation method according to the embodiment of the present invention.

Next, an example (heartbeat count calculation method) of the operation of the heartbeat count calculation apparatus 100 according to the embodiment will be described with reference to FIG. 2.

In step S101, the extraction unit 101 extracts a plurality of instantaneous heart rates in time series from biometric information obtained from a subject. The biometric information is, for example, the electrocardiographic waveform of the subject obtained by measurement using the electrocardiograph 121. In step S102, based on the difference between the latest instantaneous heart rate extracted in step S101 and the heart rate obtained last time, it is determined whether to perform switching processing (fourth step). If it is determined not to perform switching processing (NO in step S102), a heart rate is obtained, in step S103, by the same calculation processing as that performed last time. On the other hand, if it is determined to perform switching processing (YES in step S102), the switching unit 104 switches the calculation processing in step S104, and calculates a heart rate by calculation processing switched in step S105. In step S106, the heartbeat count calculation apparatus 100 determines whether an end instruction has been input. If no end instruction has been input (NO in step S106), the process returns to step S101 to continue the processing.

For example, if the first calculation unit 102 calculates the heart rate last time (second step), and the difference between this heart rate and the latest instantaneous heart rate is in the first state, the switching unit 104 determines, in step S102, to perform switching processing, switches, in step S104, from the first calculation unit 102 to the second calculation unit 103, and calculates, in step S105, the heart rate from the latest instantaneous heart rate by the second calculation unit 103 (third step).

Alternatively, for example, if the second calculation unit 103 calculates the heart rate last time (third step), and the difference between this heart rate and the latest instantaneous heart rate is in the second or third state, the switching unit 104 determines, in step S102, to perform switching processing, switches, in step S104, from the second calculation unit 103 to the first calculation unit 102, and calculates, in step S105, the heart rate from the latest instantaneous heart rate by the first calculation unit 102 (second step).

Note that in the heart rate calculation processing by the second calculation unit 103, the second coefficient starts with a value larger than the first coefficient, and is made closer to the first coefficient for each beat. This second coefficient processing is performed by the processing unit 103a. Although not shown in FIG. 2, when the difference between the latest instantaneous heart rate and the heart rate calculated by the first calculation unit 102 exceeds the set reference value, update of the heart rate can be stopped, and when the difference between the heart rate calculated at the immediately preceding time and that calculated at the current time exceeds the set reference value, the update value of the heart rate can be limited (fifth step).

Example

A more detailed description will be provided using an example. Heart rate calculation processing by a first calculation unit 102 will be referred to as the first mode hereinafter, and heart rate calculation processing by a second calculation unit 103 will be referred to as the second mode hereinafter.

In both the first and second modes, as averaging processing with an IIR filter for obtaining the heart rate of a subject from a plurality of instantaneous heart rates, a heart rate HR[n] is calculated by "HR[n]=(1−a)×HR[n−1]+a×IHR[n]" using the averaging coefficient a for instantaneous heart rates IHR[n] as n time-series data.

The averaging coefficient a takes a value of 0<a<1. As this value is smaller, a smoothing effect of suppressing a fine fluctuation in the heart rate HR[n] is higher while a delay when following a rough change is larger.

In the first mode, the averaging coefficient a is a fixed value (first coefficient). In the second mode, the averaging coefficient a is a variable value (second coefficient).

Figure 3:
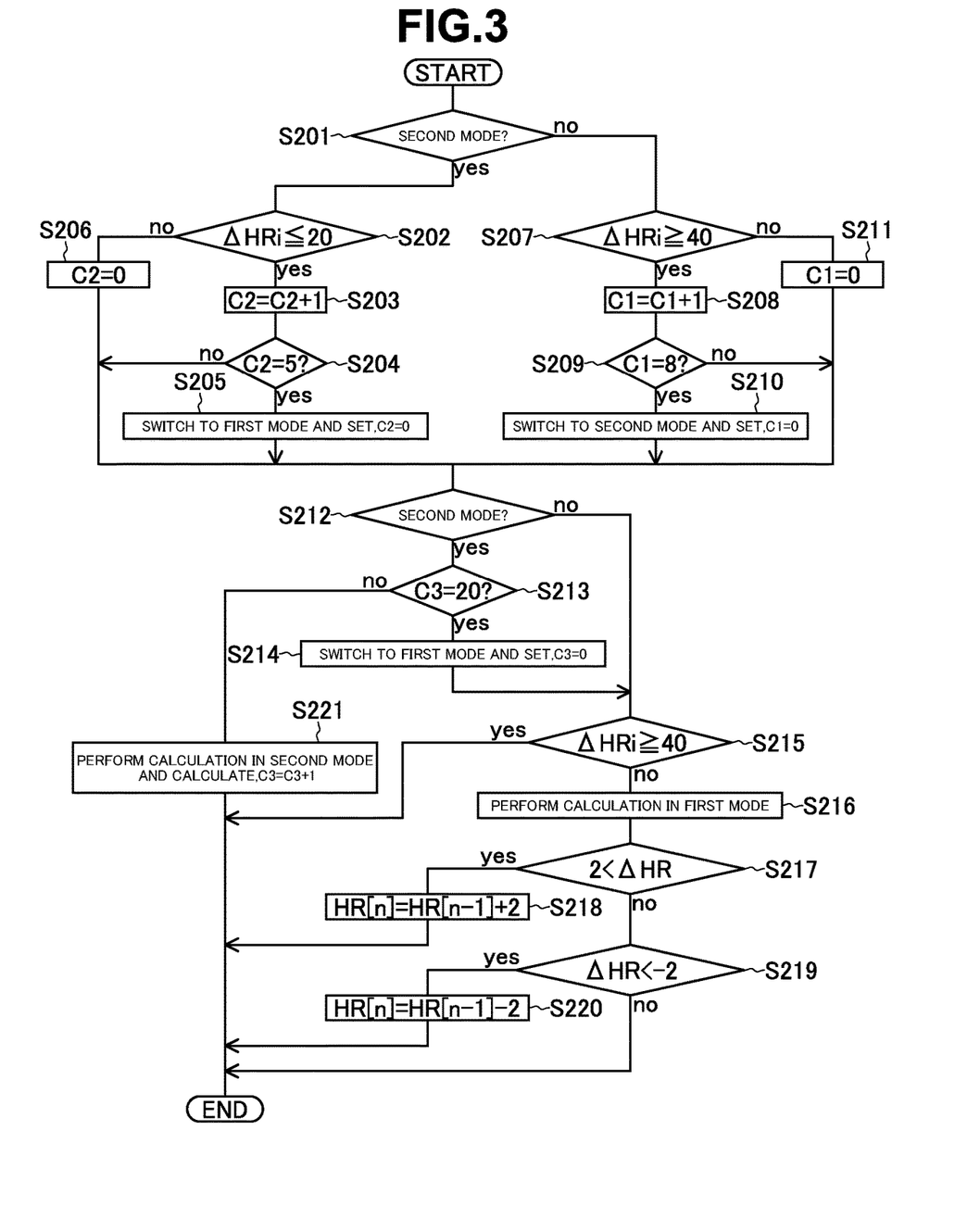
FIG. 3 is a flowchart for explaining, in more detail, the heartbeat count calculation method according to the embodiment of the present invention.

A heart rate calculation procedure according to the example under the above-described conditions will be described with reference to FIG. 3. FIG. 3 shows one cycle of a procedure of calculating a heart rate from instantaneous heart rates. Note that ΔHRi represents the absolute value of a value obtained by subtracting, from a heart rate, the latest instantaneous heart rate when the heart rate is obtained. Furthermore, ΔHR represents a value obtained by subtracting, from the heart rate calculated at the current time, a heart rate calculated at the immediately preceding time.

In step S201, it is determined whether the current mode is the second mode. If the current mode is the second mode, it is determined in step S202 whether ΔHRi is equal to or smaller than 20 (second constant). If ΔHRi is equal to or smaller than 20, 1 is added to a counted number C2 (second heartbeat count) in step S203. In step S204, it is determined whether the counted number C2 is equal to 5. If the counted number C2 is equal to 5, in step S205 the second mode is switched to the first mode and the counted number C2 is set to 0. On the other hand, if ΔHRi exceeds 20, the counted number C2 is set to 0 in step S206.

If it is determined in step S201 that the current mode is not the second mode, it is determined in step S207 whether ΔHRi is equal to or larger than 40 (first constant). If ΔHRi is equal to or larger than 40, 1 is added to a counted number C1 (first heartbeat count) in step S208. It is then determined in step S209 whether the counted number C1 is equal to 8. If the counted number C1 is equal to 8, in step S210 the first mode is switched to the second mode and the counted number C1 is set to 0. On the other hand, if ΔHRi is smaller than 40, the counted number C1 is set to 0 in step S211.

In step S212, it is determined whether the current mode is the second mode. If the current mode is the second mode, it is determined in step S213 whether a counted number C3 is equal to 20. If the counted number C3 is equal to 20, in step S214 the second mode is switched to the first mode and the counted number C3 is set to 0. If the current mode is the first mode, it is determined in step S215 whether ΔHRi is equal to or larger than 40. If ΔHRi is smaller than 40, calculation is performed in the first mode in step S216, and it is determined in step S217 whether ΔHR is larger than 2 bpm. If ΔHR is larger than 2 bpm, HR[n]=HR[n−1]+2 is set in step S218 as a heart rate update limitation. If ΔHR is equal to or smaller than 2 bpm, it is determined in step S219 whether ΔHR is smaller than −2 bpm. If ΔHR is smaller than −2 bpm, HR[n]=HR[n−1]−2 is set in step S220 as a heart rate update limitation.

If it is determined in step S213 that the counted number C3 is not equal to 20, in step S221 calculation is performed in the second mode and 1 is added to the counted number C3, thereby ending the processing of one cycle.

If it is determined in step S212 that the current mode is not the second mode (the current mode is the first mode), the process shifts to step S215.

Figure 4:
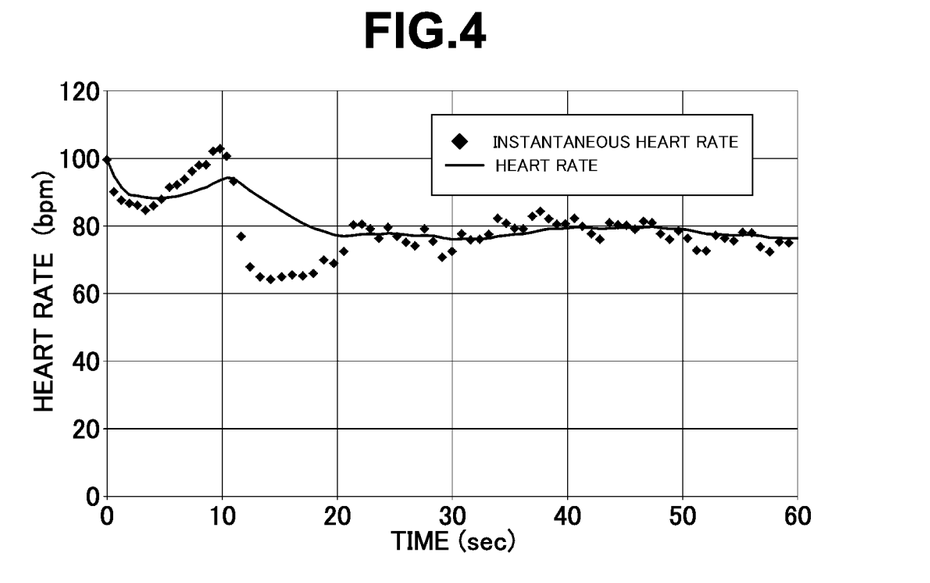
FIG. 4 is a timing chart showing a change in heartbeat count calculated in a heartbeat count calculation mode (first mode) by a first calculation unit 102 by setting an averaging coefficient a (first coefficient) to 0.1.

In the above-described processing, in the first mode, the averaging coefficient a is set to, for example, 0.1. Under this condition, as shown in FIG. 4, the heart rate HR[n] is moderately smoothed while a delay for a change is allowable.

In the second mode, the averaging coefficient a is given by, for example, "a=0.5−0.4×N/20 (N: a beat count after shifting to the second mode). That is, in the second mode, the averaging coefficient a starts with 0.5, is decreased by 0.02 for each beat, and returns to a value of 0.1 in the first mode at the 20th beat. By temporarily making the averaging coefficient a in the second mode large, the value of the instantaneous heart rate is strongly reflected, thereby obtaining an effect of accelerating convergence of the value of the heart rate.

Figure 5:
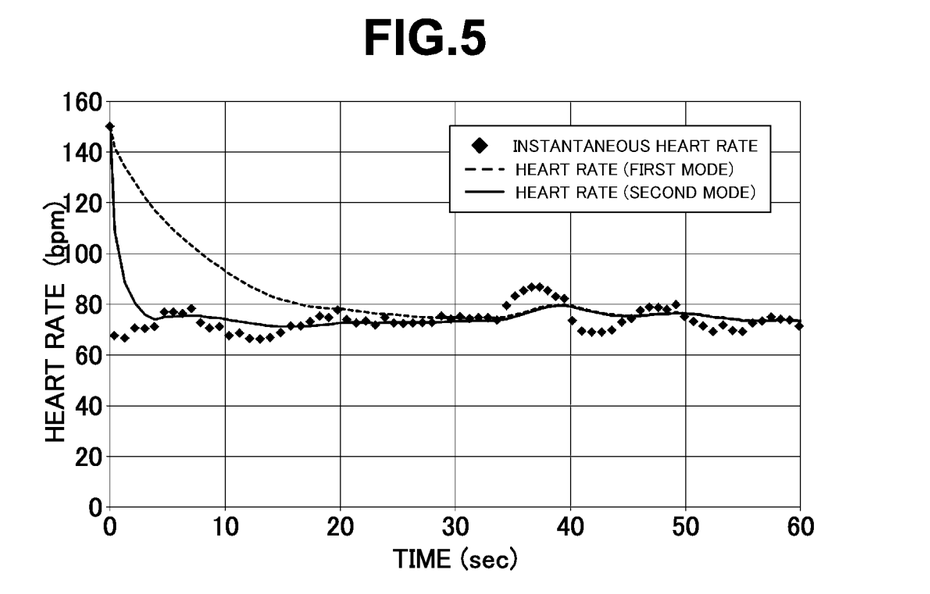
FIG. 5 is a timing chart showing a change in heartbeat count calculated in the heartbeat count calculation mode (first mode) by the first calculation unit 102 by setting the averaging coefficient a (first coefficient) to 0.1 and a change in heartbeat count calculated in a heartbeat count calculation mode (second mode) by a second calculation unit 103 by setting an averaging coefficient a (second coefficient) to a=0.5−0.4×N/20.

If the initial instantaneous heart rate is an abnormal value at the start of calculation of the heart rate, it takes time for the heart rate to approach a correct value in the first mode. However, if the second mode is set in this status, the heart rate quickly converges to the correct value, as shown in FIG. 5.

When an instantaneous heart rate largely deviated from the heart rate continues, for example, when an instantaneous heart rate deviated from the heart rate by 40 bpm or more is successively obtained eight times, the instantaneous heart rate at this time is considered to be higher in reliability than the heart rate before this time. Therefore, it is desired to discard the heart rate before this time, and calculate a heart rate based on the instantaneous heart rate at this time. To do this, under the above condition, the mode shifts to the second mode.

After the averaging coefficient a returns to a value of 0.1 in the first mode, it is appropriate to set the first mode in which the averaging coefficient a=0.1 is maintained. Furthermore, if it is considered that the difference between the heart rate and the instantaneous heart rate has converged, even when, for example, instantaneous heart rate deviated from the heart rate by 20 bpm or less is successively obtained five times, the mode shifts to the first mode, thereby making it possible to improve the smoothness of the heart rate.

Figure 6:
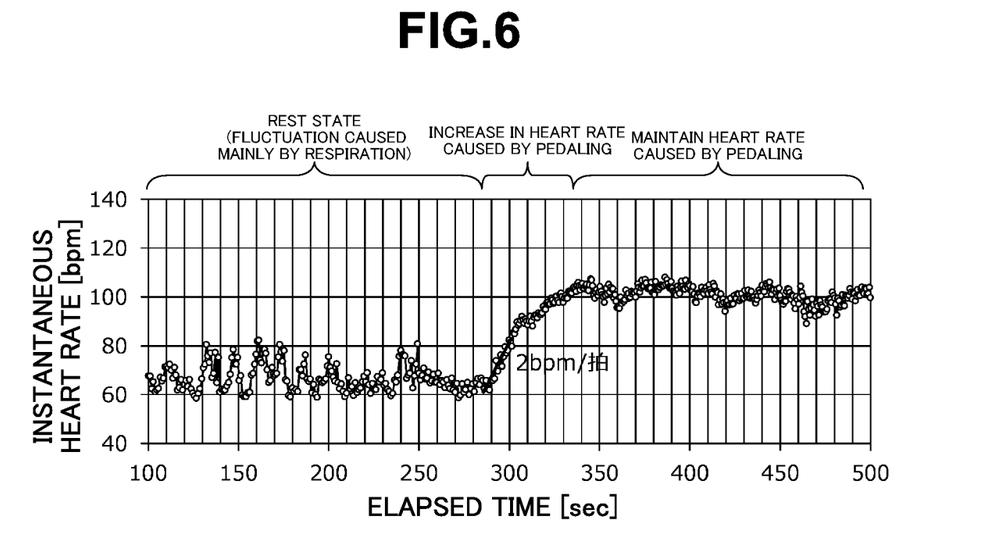
FIG. 6 is a timing chart showing a change in heartbeat count of a human when suddenly performing an exercise such as pedaling with full force from a rest state.

Note that when, for example, suddenly performing an exercise such as pedaling with full force from a rest state, the heart rate of a human increases at a rate of about 2 bpm/beat at most. FIG. 6 shows this state. Conversely, it is hardly considered that the heart rate increases at a rate exceeding 2 bpm/beat. Therefore, if the change amount of the heart rate is provided with an upper limit of 2 bpm/beat, it is possible to prevent the obtained heart rate from being an abnormal value.

As processing at each time when the instantaneous heart rate is largely deviated from the heart rate, for example, if the difference between the instantaneous heart rate and the heart rate is equal to or larger than 40 bpm, it is appropriate to consider the instantaneous heart rate as an abnormal value, and this value is discarded not to update the heart rate. However, this corresponds to the first mode, and the same does not apply to the second mode as a period for recovering the state from the abnormal state.

Figure 7:
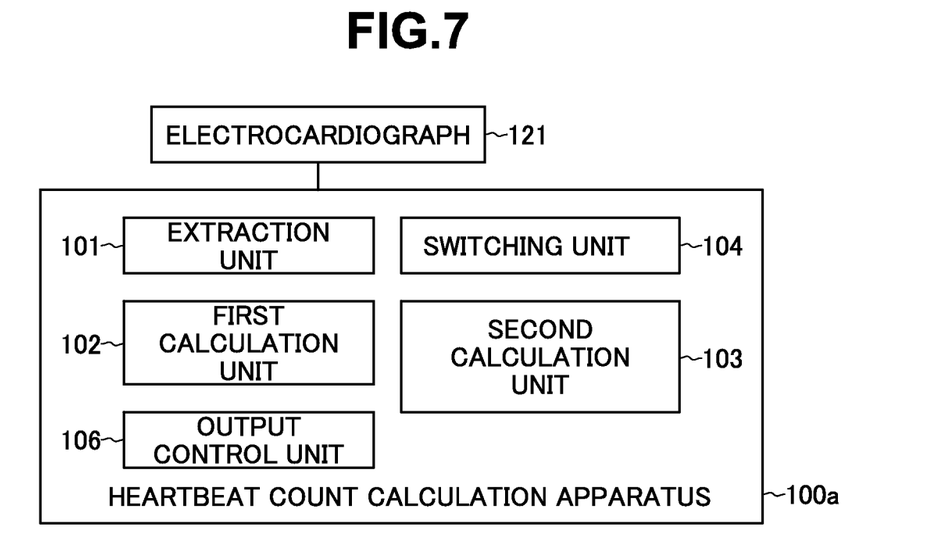
FIG. 7 is a block diagram showing the arrangement of another heartbeat count calculation apparatus 100a according to the embodiment of the present invention.

Another heartbeat count calculation apparatus 100a according to the embodiment of the present invention will be described next with reference to FIG. 7. The heartbeat count calculation apparatus 100a includes an extraction unit 101, a first calculation unit 102, a second calculation unit 103, and a switching unit 104. These components are the same as those of the above-described heartbeat count calculation apparatus 100.

The heartbeat count calculation apparatus 100a includes an output control unit 106. The output control unit 106 determines, as an abnormal period, a period during which the second calculation unit 103 calculates a heart rate, a period during which the difference between the latest instantaneous heart rate and a heart rate calculated by the first calculation unit 102 exceeds a reference value, or a period during which the calculated heart rate falls within a set abnormal range, and stops output of the heart rate during the abnormal period. If, for example, the difference between the instantaneous heart rate and the heart rate is equal to or larger than 40 bpm, the calculated heart rate may include an abnormal value or its influence. Alternatively, the calculated heart rate may extremely be deviated from an ordinary value to become an abnormal value (falls within the set abnormal range) such as 0. In this case, an abnormal period is determined to stop output of the calculated heart rate.

Furthermore, the output control unit 106 can be configured to determine, as the second abnormal period, a period until an abnormal period is determined again within a determination period set after the abnormal period, and stop output of the heart rate during the second abnormal period. For example, if an abnormal period is determined again within 30 sec after an abnormal period is determined, a period from the last determination of the abnormal period to this determination of the abnormal period is set as the second abnormal period, and output of the heart rate is stopped during the second abnormal period.

If the heart rate obtained during the abnormal period falls within an allowable range set with respect to the heart rate obtained during a period other than the abnormal period, the output control unit 106 outputs the heart rate (heartbeat count). Even during the abnormal period, the difference between the obtained heart rate and the heart rate obtained during the period other than the abnormal period falls within, for example, a range of ±10 bpm, the obtained heart rate is adopted as an output value.

A heartbeat count calculation method by the heartbeat count calculation apparatus 100a can include the following steps in addition to the steps described with reference to FIG. 2. It is possible to set, as an abnormal period, a period during which the second calculation unit 103 (second step) calculates a heart rate, a period during which the difference between the latest instantaneous heart rate and the heart rate calculated by the first calculation unit 102 (first step) exceeds the reference value, or a period during which the calculated heart rate falls within the set abnormal range, and stop output of the heart rate during the abnormal period (sixth step). If the heart rate obtained during the abnormal period falls within the allowable range set with respect to the heart rate obtained during the period other than the abnormal period, it is possible to output the heart rate (heartbeat count) (seventh step). Furthermore, it is possible to determine, as the second abnormal period, a period until an abnormal period is determined again within a determination period set after the abnormal period, and stop output of the heart rate during the second abnormal period (eighth step).

Examples of determination of the abnormal period will be described below with reference to FIGS. 8A, 8B, 8C, 8D, and 8E. Referring to FIGS. 8A, 8B, 8C, 8D, and 8E, obtained heart rates are represented by open circles.

Figure 8A:
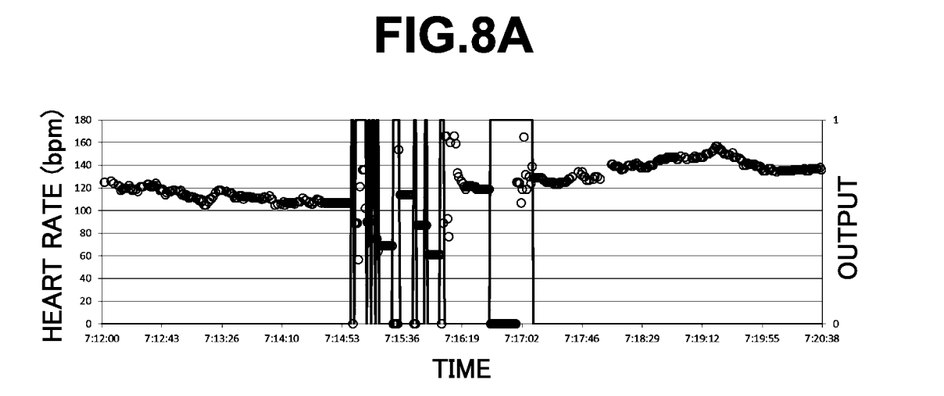
FIG. 8A is an explanatory timing chart showing an example of determination of an abnormal period.

In FIG. 8A, a result of determining whether the obtained heart rate is a normal value or an abnormal value is indicated by solid lines. If the heart rate is a normal value, 0 is determined, and if the heart rate is an abnormal value, 1 is determined. Time at which 1 is determined falls within an abnormal period, and thus the heart rate is not output.

Figure 8B:
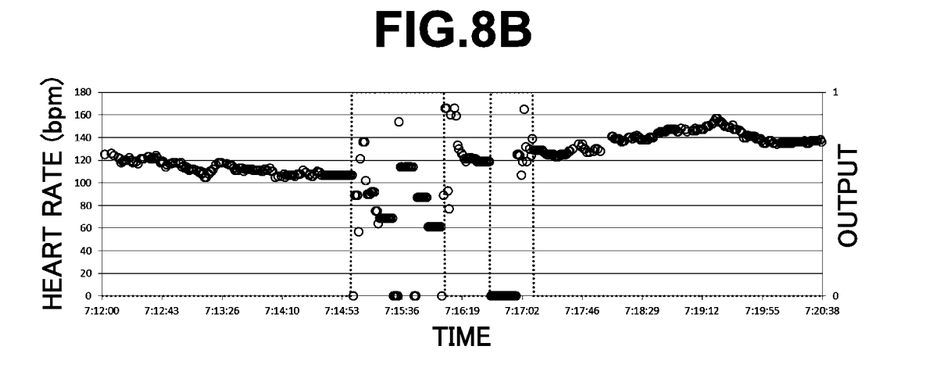
FIG. 8B is an explanatory timing chart showing an example of determination of an abnormal period.
Figure 8C:
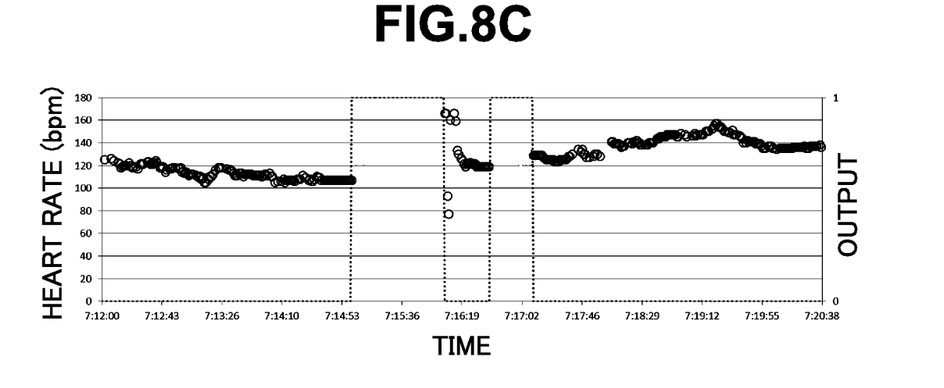
FIG. 8C is an explanatory timing chart showing an example of determination of an abnormal period.

In FIG. 8B, when an abnormal period is determined again within 30 see after an abnormal period is determined, a result of determining, as an abnormal value (a value of 1), an entire period from the last determination of the abnormal period to this determination of the abnormal period is indicated by dotted lines. The period indicated by the dotted lines during which a value of 1 is determined is set as the second abnormal period for a heart rate acquisition period, and the obtained heart rate is not output during this period, as shown in FIG. 8C.

Figure 8D:
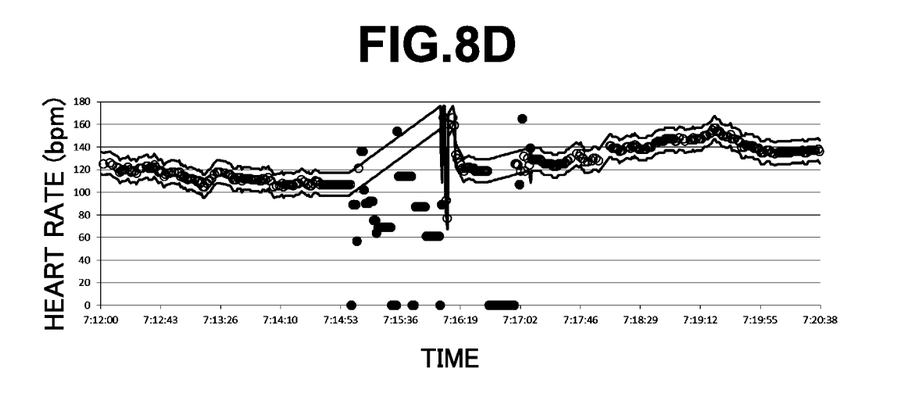
FIG. 8D is an explanatory timing chart showing an example of determination of an abnormal period.
Figure 8E:
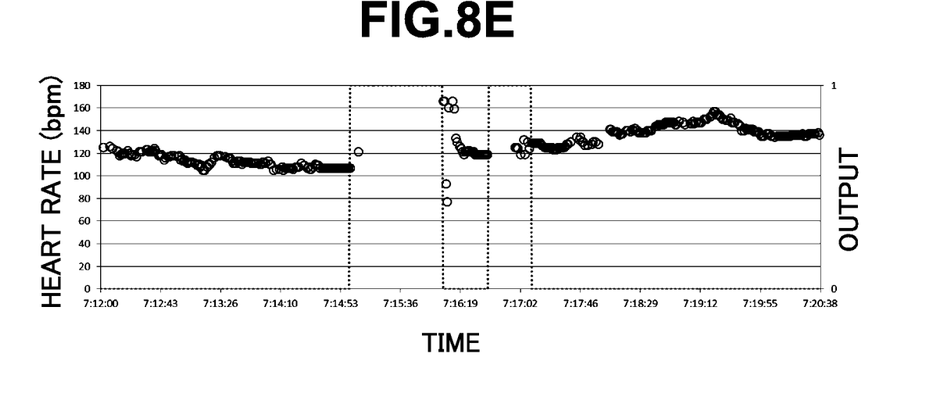
FIG. 8E is an explanatory timing chart showing an example of determination of an abnormal period.

In FIG. 8D, a range of ±10 from each heart rate value except for the heart rates obtained during the above-described second abnormal period is indicated by solid lines. Since not all the heart rates during the second abnormal period are abnormal, the heart rate within this range can be output, as shown in FIG. 8E.

In the above description, the electrocardiographic waveform of a living body is used as biometric information and a heart rate is used as a heartbeat count. However, the present invention is not limited to this. Information concerning a pulse can be used as biometric information and a pulse rate can be used as a heartbeat count. For example, a pulse waveform is obtained in time series as biometric information by irradiating the skin with light and measuring reflected light. Since the light absorption amount of blood changes depending on the pulse to change the reflected light intensity, it is possible to measure the pulse rate from the change in reflection intensity. By forming, for example, an arrangement in which a semiconductor light emitting element is used as a light source and a photodiode measures reflected light, a measurement apparatus can be downsized, thereby obtaining a wristband type sensor. Such downsizing makes it possible to very easily use the measurement apparatus by mounting it on a subject.

Furthermore, for example, it is possible to use, as a heartbeat count, a pulse rate obtained by measuring a change in color of the skin surface of the face or the like. Since the amount of light obtained when the skin is irradiated with sunlight or illumination light and reflects the light changes depending on a pulse, a pulse rate can be measured using a result of capturing the change by a camera or the like. In this case, it is possible to obtain an advantage that it is possible to measure a pulse rate in a place away from the subject without mounting anything on the subject.

Figure 9:
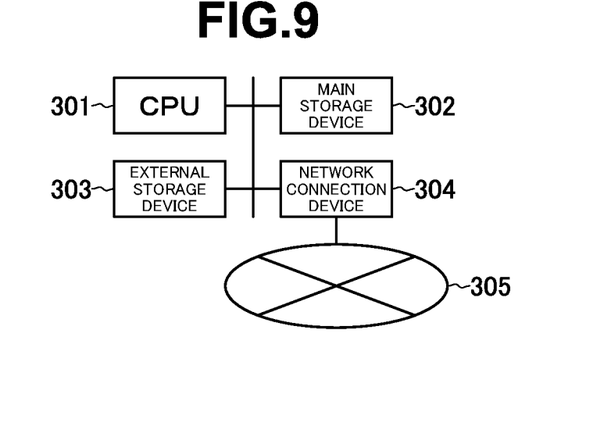
FIG. 9 is a block diagram showing the hardware arrangement of the heartbeat count calculation apparatus according to embodiments of the present invention.

Note that the heartbeat count calculation apparatus according to the above-described embodiment is a mobile computer apparatus including a CPU (Central Processing Unit) 301, a main storage device 302, an external storage device 303, and a network connection device 304, as shown in FIG. 9. Each of the above-described functions is implemented when the CPU 301 operates by a program loaded into the main storage device 302. Note that the network connection device 304 is connected to a network 305. The respective functions can also be distributed to a plurality of computer apparatuses.

The heartbeat count calculation apparatus according to the above-described embodiment can be formed by a PLD (Programmable Logic Device) such as an FPGA (Field-Programmable Gate Array). For example, the storage unit, the extraction unit, the first calculation unit, the second calculation unit, and the switching unit are provided as circuits in the logic elements of an FPGA, the FPGA can be made to function as the heartbeat count calculation apparatus. Each of the storage unit, the extraction unit, the first calculation unit, the second calculation unit, and the switching unit is written in the FPGA by connecting a predetermined writing device.

As described above, according to embodiments of the present invention, the first calculation unit that calculates a heartbeat count from a plurality of instantaneous heartbeat counts by averaging processing with an IIR filter using the first coefficient of a fixed value smaller than 1 and the second calculation unit that calculates the heartbeat count from the plurality of instantaneous heartbeat counts by averaging processing with an IIR filter using the second coefficient of a variable value smaller than 1 are switched based on the difference between the precedingly calculated heartbeat count and the latest instantaneous heartbeat count. As a result, according to embodiments of the present invention, even if the instantaneous heartbeat counts include an abnormal value, it is possible to calculate a heartbeat count appropriately.

Note that the present invention is not limited to the above-described embodiment, and it is obvious that many modifications and combinations can be made by a person with normal knowledge in the field within the technical scope of the present invention.

Explanation of the Reference Numerals and Signs

100 . . . heartbeat count calculation apparatus,
101 . . . extraction unit,
102 . . . first calculation unit,
103 . . . second calculation unit,
104 . . . switching unit,
105 . . . update stopping unit,
106 . . . output control unit, 121 . . . electrocardiograph.

The invention claimed is:

1. A heartbeat count calculation apparatus comprising:
    an extractor configured to extract a plurality of instantaneous heartbeat counts in time series from biometric information;
    a first calculator configured to calculate a heartbeat count from the plurality of instantaneous heartbeat counts by averaging processing with a first Infinite Impulse Response (IIR) filter;
    a second calculator configured to calculate the heartbeat count from the plurality of instantaneous heartbeat counts by averaging processing with a second IIR filter having a faster response than the first IIR filter; and
    a switch configured to switch between the first calculator and the second calculator based on a difference between the heartbeat count calculated by the first calculator or the second calculator and a latest instantaneous heartbeat count extracted by the extractor;
    wherein the first IIR filter uses a first coefficient of a fixed value smaller than 1;
    wherein the second IIR filter uses a second coefficient of a variable value smaller than 1; and
    wherein the second calculator includes a coefficient processor configured to:
        start the second coefficient with a value larger than the first coefficient; and adjust the second coefficient closer to the first coefficient for each heartbeat.

2. The heartbeat count calculation apparatus according to claim 1, wherein,
in a first state, the switch switches from the first calculator to the second calculator, the first state being a state in which the difference between the latest instantaneous heartbeat count and the heartbeat count calculated by the first calculator is continuously not smaller than a set first constant for a set first heartbeat count, and
in a second state or a third state, the switch switches from the second calculator to the first calculator, the second state being a state in which the difference between the latest instantaneous heartbeat count and the heartbeat count calculated by the second calculator is continuously not larger than a set second constant for a set second heartbeat count, the third state being a state in which the second coefficient is equal to the first coefficient.

3. The heartbeat count calculation apparatus according to claim 1, wherein the biometric information is an electrocardiographic waveform of a living body, and the heartbeat count is a heart rate.

4. The heartbeat count calculation apparatus according to claim 1, wherein the biometric information is information concerning a pulse, and the heartbeat count is a pulse rate.

5. A heartbeat count calculation apparatus comprising:
an extractor configured to extract a plurality of instantaneous heartbeat counts in time series from biometric information;
a first calculator configured to calculate a heartbeat count from the plurality of instantaneous heartbeat counts by averaging processing with a first Infinite Impulse Response (IIR) filter;
a second calculator configured to calculate the heartbeat count from the plurality of instantaneous heartbeat counts by averaging processing with a second IIR filter having a faster response than the first IIR filter;
a switch configured to switch between the first calculator and the second calculator based on a difference between the heartbeat count calculated by the first calculator or the second calculator and a latest instantaneous heartbeat count extracted by the extractor; and
an update stopper configured to:
stop updating the heartbeat count when the difference between the latest instantaneous heartbeat count and the heartbeat count calculated by the first calculator exceeds a set reference value; and
limit an update value of the heartbeat count when a difference between the heartbeat count calculated at an immediately preceding time by the first calculator and the heartbeat count calculated at a current time by the first calculator exceeds the set reference value.

6. The heartbeat count calculation apparatus according to claim 5, wherein the biometric information is an electrocardiographic waveform of a living body, and the heartbeat count is a heart rate.

7. The heartbeat count calculation apparatus according to claim 5, wherein the biometric information is information concerning a pulse, and the heartbeat count is a pulse rate.

8. A heartbeat count calculation apparatus comprising:
an extractor configured to extract a plurality of instantaneous heartbeat counts in time series from biometric information;
a first calculator configured to calculate a heartbeat count from the plurality of instantaneous heartbeat counts by averaging processing with a first Infinite Impulse Response (IIR) filter;
a second calculator configured to calculate the heartbeat count from the plurality of instantaneous heartbeat counts by averaging processing with a second IIR filter having a faster response than the first IIR filter;
a switch configured to switch between the first calculator and the second calculator based on a difference between the heartbeat count calculated by the first calculator or the second calculator and a latest instantaneous heartbeat count extracted by the extractor; and
an output controller configured to:
determine, as an abnormal period, a period during which the second calculator calculates the heartbeat count, a period during which the difference between the latest instantaneous heartbeat count and the heartbeat count calculated by the first calculator exceeds a set reference value, or a period during which the heartbeat count calculated by the first calculator the second calculator falls within a set abnormal range; and
stop output of the heartbeat count during the abnormal period.

9. The heartbeat count calculation apparatus according to claim 8, wherein, in response to the heartbeat count obtained during the abnormal period falls within an allowable range set with respect to a heartbeat count obtained during a period other than the abnormal period, the output controller outputs the heartbeat count obtained during the abnormal period.

10. The heartbeat count calculation apparatus according to claim 8, wherein the biometric information is an electrocardiographic waveform of a living body, and the heartbeat count is a heart rate.

11. The heartbeat count calculation apparatus according to claim 8, wherein the biometric information is information concerning a pulse, and the heartbeat count is a pulse rate.

12. A heartbeat count calculation method comprising:
extracting a plurality of instantaneous heartbeat counts in time series from biometric information;
obtaining a heartbeat count with a first process, the first process obtains the heartbeat count from the plurality of instantaneous heartbeat counts by averaging processing with a first Infinite Impulse Response (IIR) filter;
obtaining a heartbeat count with a second process, the second process obtains the heartbeat count from the plurality of instantaneous heartbeat counts by averaging processing with a second IIR filter, the second IIR filter having a faster response than the first IIR filter; and
switching between the first process and the second process to obtain the heartbeat count based on a difference between an extracted latest instantaneous heartbeat count and the heartbeat count obtained with the first process or the second process;
wherein the first IIR filter uses a first coefficient of a fixed value smaller than 1;
wherein the second IIR filter uses a second coefficient of a variable value smaller than 1; and
wherein the second process comprises:
starting the second coefficient at a value larger than the first coefficient; and
adjusting the second coefficient closer to the first coefficient for each heartbeat.

13. The heartbeat count calculation method according to claim 12, wherein switching between the first process and the second process comprises:
in a first state, switching from the first process the second process, the first state being a state in which the difference between the latest instantaneous heartbeat count and the heartbeat count calculated by the first process is continuously not smaller than a set first constant for a set first heartbeat count, and
in a second state or a third state, switching from the second process to the first process, the second state being a state in which the difference between the latest instantaneous heartbeat count and the heartbeat count calculated by the second process is continuously not larger than a set second constant for a set second heartbeat count, the third state being a state in which the second coefficient is equal to the first coefficient.

14. The heartbeat count calculation method according to claim 12, wherein the biometric information is an electrocardiographic waveform of a living body, and the heartbeat count is a heart rate.

15. The heartbeat count calculation method according to claim 12, wherein the biometric information is information concerning a pulse, and the heartbeat count is a pulse rate.

16. A heartbeat count calculation method comprising:
extracting a plurality of instantaneous heartbeat counts in time series from biometric information;
obtaining a heartbeat count with a first process, the first process obtains the heartbeat count from the plurality of instantaneous heartbeat counts by averaging processing with a first Infinite Impulse Response (IIR) filter;
obtaining a heartbeat count with a second process, the second process obtains the heartbeat count from the plurality of instantaneous heartbeat counts by averaging processing with a second IIR filter, the second IIR filter having a faster response than the first IIR filter;
switching between the first process and the second process to obtain the heartbeat count based on a difference between an extracted latest instantaneous heartbeat count and the heartbeat count obtained with the first process or the second process;
stop updating the heartbeat count when the difference between the latest instantaneous heartbeat count and the heartbeat count obtained in the second process exceeds a set reference value; and
limiting an update value of the heartbeat count when a difference between the heartbeat count calculated at an immediately preceding time in the first process and the heartbeat count calculated at a current time in the first process exceeds the set reference value.

17. The heartbeat count calculation method according to claim 16, wherein the biometric information is an electrocardiographic waveform of a living body, and the heartbeat count is a heart rate.

18. The heartbeat count calculation method according to claim 16, wherein the biometric information is information concerning a pulse, and the heartbeat count is a pulse rate.

19. A heartbeat count calculation method comprising:
extracting a plurality of instantaneous heartbeat counts in time series from biometric information;
obtaining a heartbeat count with a first process, the first process obtains the heartbeat count from the plurality of instantaneous heartbeat counts by averaging processing with a first Infinite Impulse Response (IIR) filter;
obtaining a heartbeat count with a second process, the second process obtains the heartbeat count from the plurality of instantaneous heartbeat counts by averaging processing with a second IIR filter, the second IIR filter having a faster response than the first IIR filter;
switching between the first process and the second process to obtain the heartbeat count based on a difference between an extracted latest instantaneous heartbeat count and the heartbeat count obtained with the first process or the second process;
determining, as an abnormal period, a period during which the heartbeat count is obtained in the second process, a period during which the difference between the latest instantaneous heartbeat count and the heartbeat count obtained in the first process exceeds a set reference value, or a period during which the heartbeat count falls within a set abnormal range; and
stopping output of the heartbeat count during the abnormal period.

20. The heartbeat count calculation method according to claim 19, wherein the biometric information is an electrocardiographic waveform of a living body, and the heartbeat count is a heart rate.

21. The heartbeat count calculation method according to claim 19, wherein the biometric information is information concerning a pulse, and the heartbeat count is a pulse rate.

22. The heartbeat count calculation method according to claim 19, further comprising outputting the heartbeat count when the heartbeat count obtained during the abnormal period falls within an allowable range set with respect to a heartbeat count obtained during a period other than the abnormal period.

* * * * *